United States Patent [19]

Tsai et al.

[11] 4,312,746
[45] Jan. 26, 1982

[54] CATALYTIC PRODUCTION OF OCTAHYDROPHENANTHRENE-ENRICHED SOLVENT

[75] Inventors: Shirley C. Tsai; Howard G. McIlvried, III, both of Pittsburgh, Pa.

[73] Assignee: Gulf Research & Development Company, Pittsburgh, Pa.

[21] Appl. No.: 118,762

[22] Filed: Feb. 5, 1980

[51] Int. Cl.³ .......................... C10G 45/00; C07C 5/10
[52] U.S. Cl. .................................... 208/143; 208/144; 208/145; 208/8 LE; 585/268; 585/270; 252/441; 252/470
[58] Field of Search .................. 208/145, 143, 144; 585/268, 270

[56] References Cited

U.S. PATENT DOCUMENTS

| | | | |
|---|---|---|---|
| 3,488,278 | 1/1970 | Nelson | 208/10 |
| 3,503,864 | 3/1970 | Nelson | 208/10 |
| 3,505,203 | 4/1970 | Nelson | 208/8 |
| 3,726,785 | 4/1973 | Keller | 208/8 |
| 3,867,275 | 2/1975 | Gleim | 208/8 |
| 3,884,794 | 5/1975 | Bull | 208/8 |
| 4,045,328 | 8/1977 | Green | 208/8 |
| 4,048,054 | 9/1977 | Green | 208/8 |
| 4,080,286 | 3/1978 | Yanik | 252/469 |
| 4,128,505 | 12/1978 | Mikovsky | 252/469 |

OTHER PUBLICATIONS

Ruberto et al., "Structural Aspects of Sub-Bituminous Coal Deduced from Salvation Studies 2. Hydrophenanthrene solvents", *Fuel*, (1977), vol. 56, pp. 25-31.
Shabtai et al., "ACS Preprint Fuel Chemistry Division", vol 23, No. 1, (1978), pp. 107-113.
Huang et al., "ACS Preprint Fuel Chemistry Division", vol. 21, No. 5, (1976), pp. 228-242.
Curran et al., "I. & E.C. Process Design and Development", vol. 6, No. 2, Apr. (1967), pp. 166-173.

*Primary Examiner*—Brian E. Hearn
*Attorney, Agent, or Firm*—Deane E. Keith; Forrest D. Stine; Alvin E. Ring

[57] ABSTRACT

The OHP content of an OHP- and THP-containing solvent is enriched by contacting the solvent with hydrogen in the presence of a supported catalyst comprising Group VIB and Group VIII metals under conditions to increase the OHP/THP ratio in the solvent to a level greater than 0.4 and preferably greater than 1. The preferred catalyst contains tungsten where it is desired to provide an OHP/THP ratio greater than 1 in the OHP-enriched solvent, and also contains titanium to improve the hydrogen selectivity of the catalyst so as to enhance the preservation of aromatics in the hydrogenated solvent. The OHP-enriched solvent provides increased solvation of coal and improved yields of liquid fuel product in a coal liquefaction process which utilizes the solvent.

19 Claims, 4 Drawing Figures

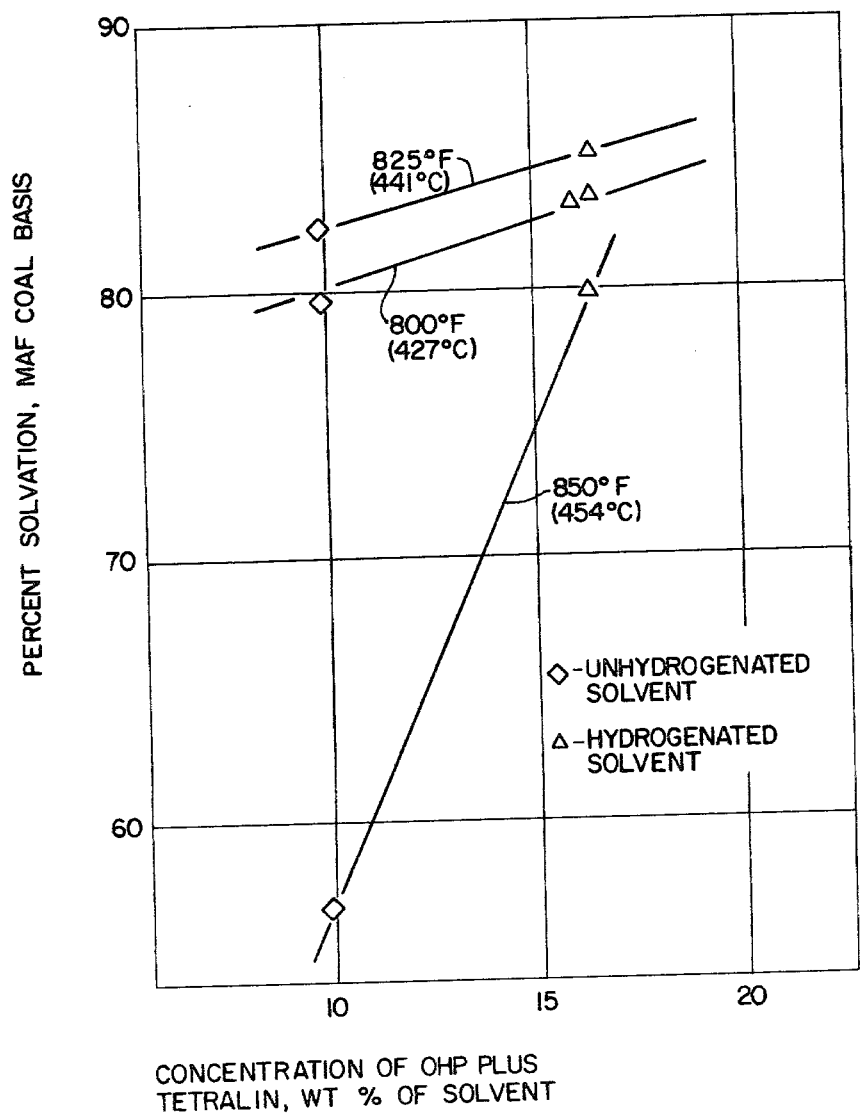

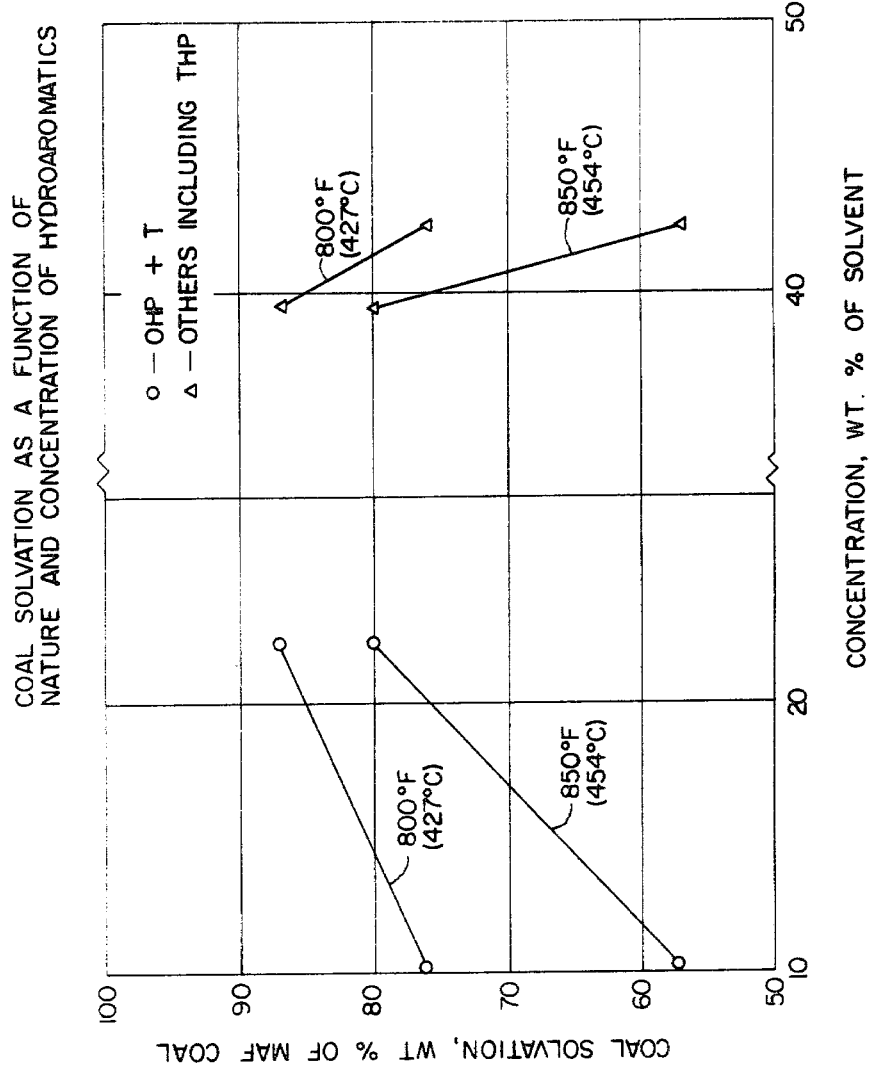

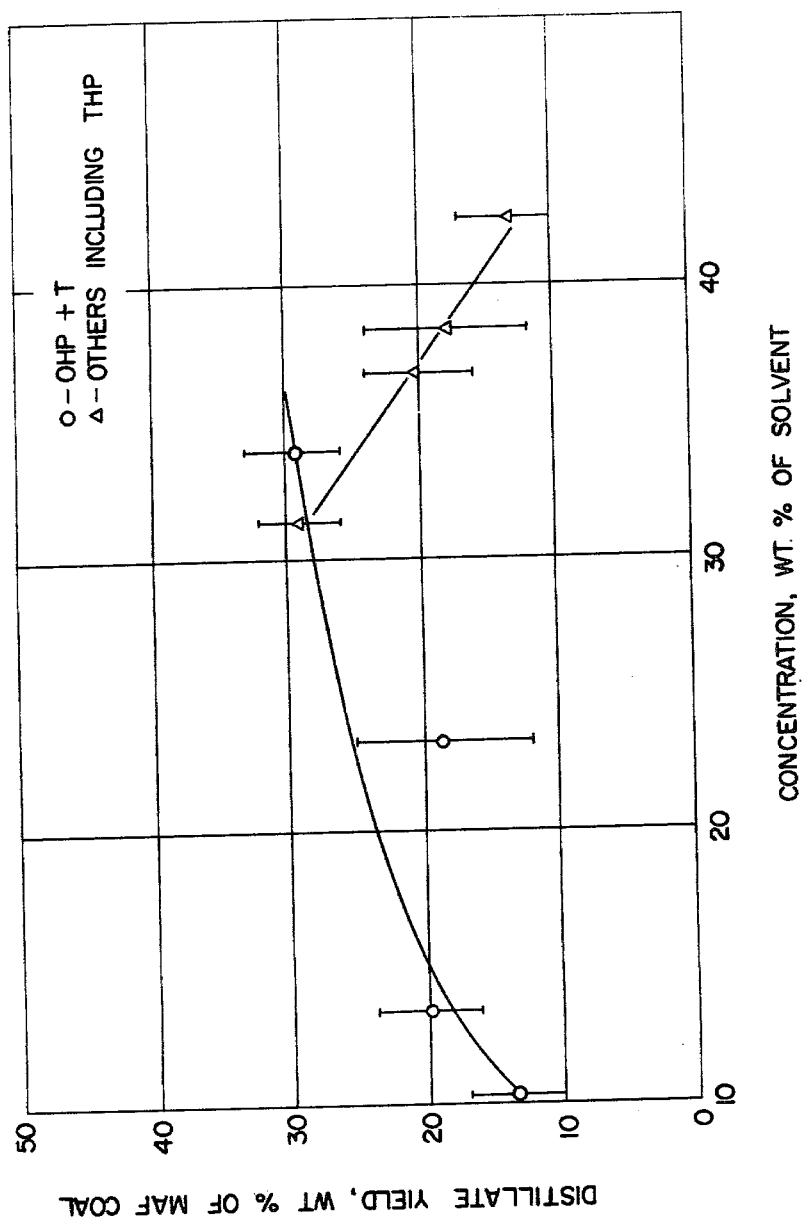

CATALYTIC PRODUCTION OF OCTAHYDROPHENANTHRENE-ENRICHED SOLVENT

CROSS-REFERENCES TO RELATED APPLICATIONS

Reference is made to the following U.S. applications filed on even date:

U.S. patent application Ser. No. 118,859 to Shirley C. Tsai and Howard G. McIlvried, III entitled "Coal Liquefaction Process Employing Octahydrophenanthrene-Enriched Solvent".

U.S. patent application Ser. No. 118,860 to Shirley C. Tsai and Howard G. McIlvried, III entitled "Solvent Refining Of Coal Using Octahydrophenanthrene-Enriched Solvent and Mineral Recycle".

The foregoing applications are hereby incorporated by reference.

FIELD OF THE INVENTION

The present invention relates to a process for producing a hydrogen donor solvent for use in the production of a hydrocarbonaceous liquid fuel from ash-containing raw coal. More particularly, this invention relates to a catalytic hydrogenation process for producing an octahydrophenanthrene-enriched solvent employing a supported catalyst comprising Group VIB and Group VIII metals.

DESCRIPTION OF THE PRIOR ART

Coal solvation/liquefaction processes are well known in which ash-containing raw coal is contacted with a solvent containing hydrogen-donor compounds to produce liquid fuels. In such processes the valuable liquid fuel is produced by depolymerization of the coal. The depolymerization occurs through various reactions, such as the removal of heteroatoms, including sulphur and oxygen, and through thermal fracture of the coal to form free radicals. The free radicals are prevented from repolymerizing through the transfer of hydrogen from solvent hydrogen donor compounds to the free radicals which become end-capped and thus stabilized.

Various hydroaromatic compounds have been suggested for use as hydrogen donors in the solvent including partially hydrogenated naphthalenes, acenaphthalenes, anthracenes, penanthrenes, and the like. U.S. Pat. No. 4,048,054 discloses various hydroaromatic compounds including di-, tetra- and octahydroanthracenes as constituting at least 50 weight percent of the hydrogen donor solvent, while U.S. Pat. No. 3,867,275 expresses a preference for dihydrophenanthrene, dihydroanthracene and tetrahydroanthracene. Curran et al in "I&EC Process Design and Development", Vol. 6, No. 2, April, 1967, pps. 166 to 173 (Table IV on p. 168), disclose dihydrophenanthrene as being an even better hydrogen donor than Tetralin (tetrahydronaphthalene), which is considered one of the best hydrogen donors, but further disclose that the fully saturated perhydrophenanthrene was the worst hydrogen donor of those tested.

SUMMARY OF THE INVENTION

It has now been found that an octahydrophenanthrene-enriched hydrogen donor solvent can be produced by hydrogenating an octahydrophenanthrene and tetrahydrophenanthrene-containing solvent, which is preferably derived from coal liquids, in the presence of hydrogen and a supported catalyst comprising Group VIB and Group VIII metals or their oxides and sulfides. The resulting octahydrophenanthrene-enriched solvent provides improved coal solvation and distillate liquid yields when used as the solvent in a coal solvation/liquefaction process.

Normally, phenanthrenes are present in greater quantity than anthracenes in coal-derived liquids. However, phenanthrenes and corresponding anthracenes are not normally distinguishable from one another because of their closeness in boiling point. Thus, the expression "OHP" will be used herein to mean octahydrophenanthrene, its alkyl homologues; octahydroanthracene, its alkyl homologues; or mixtures thereof. Similarly, "THP" will mean tetrahydrophenanthrene, its alkyl homologues; tetrahydroanthracene, its alkyl homologues; or mixtures thereof. Likewise, "P" will be understood to mean non-hydrogenated phenanthrene, its alkyl homologues; non-hydrogenated anthracene, its alkyl homologues; or mixtures thereof.

The process of the present invention comprises contacting a solvent containing OHP and THP in a ratio of OHP/THP below 0.4 with hydrogen in the presence of a supported catalyst comprising Group VIB and Group VIII metals or their oxides or sulfides under conditions to increase the weight ratio of OHP/THP to a value greater than 0.4.

The process solvent produced in a coal solvation/liquefaction process which does not employ a downstream catalytic hydrogenation zone normally contains OHP and THP in a weight ratio of OHP/THP well below 0.4, e.g., 0.19. Thus, according to the present invention, the OHP content of the process solvent is increased by subjecting the solvent to downstream catalytic hydrogenation to convert a portion of the THP present in the solvent to OHP utilizing a supported catalyst containing Group VIB and Group VIII metals, as oxides and/or sulfides, in the presence of hydrogen and under conditions which will result in an OHP-enriched solvent containing OHP and THP in a weight ratio greater than 0.4, and preferably greater than 1, but below 10 or 15. Additionally, the catalytically hydrogenated solvent should contain at least 5 weight percent OHP, and preferably at least 10 weight percent OHP.

A preferred catalyst for producing the OHP-enriched solvent according to the present invention is a tungsten-containing catalyst, and more preferably a nickel- and tungsten-containing catalyst, such as NiWF on an alumina support. Also, it is especially preferred to include titanium in the catalyst in order to improve hydrogen selectivity as evidenced by an enhanced preservation of an aromatic segment in the molecules of the hydrogenated solvent. Thus, an especially preferred catalyst is NiTiMoW on alumina.

Surprisingly, it has been found that in a coal solvation/liquefaction process wherein OHP and THP are present in the process solvent, it is the more saturated OHP which acts as the significant hydrogen donor material as evidenced by a significant decrease in OHP concentration during liquefaction by conversion to THP while concomitantly the less-saturated THP remains relatively inactive as a hydrogen donor and does not contribute significantly to hydrogen transfer in the presence of an adequate quantity of OHP. In fact, in the presence of OHP, the concentration of THP has been found to actually increase during coal solvation indicating a considerable conversion of OHP to THP, without a comparable dehydrogenative conversion of the THP to P or other aromatic. This is indicated by a level of P, which has less donor hydrogen than THP, below 10 weight percent, and by the substantial absence of DHP (dihydrophenanthrene, its alkyl homologues; dihydroanthracene, its alkyl homologues; or mixtures thereof) in the liquefaction product.

By utilizing a solvent containing both OHP and THP in which the ratio of OHP/THP is greater than 0.4 and in which OHP constitues at least 5 weight percent of the solvent, coal solvation is improved and hydrocracking increased with an attendant higher yield of the desired liquid product, as compared with a process using a solvent which contains smaller amounts of OHP and correspondingly greater amounts of THP. In this process, hydrogen donation from the THP is not favored so that the effluent from the liquefaction zone will comprise less than 15 weight percent P, e.g., between about 7 and about 15 weight percent, generally, and preferably between about 5 and about 10 weight percent P.

Although the hydrogen donor properties of the solvent are greatly improved by increasing the ratio of OHP to THP in the solvent, it is not desirable to convert all of the THP present in the solvent to OHP, since this would result in increased or nonselective consumption of hydrogen and loss of hydroaromatics to form non-donor compounds such as perhydrophenanthrenes and perhydroanthrenes. Accordingly, although the OHP to THP ratio should be greater than 0.4 or 1 in the solvent, there should remain at least 1 weight percent THP, for example, 5 to 30 weight percent THP, and preferably 10 to 20 weight percent THP in the solvent. Although hydrogen is consumed in the catalytic step to increase the ratio of OHP to THP in accordance with this invention, we have found that the increased ratio of OHP to THP induces a reduction in hydrogen consumption in the non-catalytic coal liquefaction step, so that there is a net reduction in hydrogen consumption in the total process as compared to a process wherein coal solvation occurs with a solvent having a lower OHP to THP ratio. It was unexpected that the conversion of THP, which is a known advantageous hydrogen donor, to OHP, which requires hydrogen consumption, can result in a net savings of hydrogen for the overall process. Such savings in hydrogen provides a significant economic advantage in view of the high cost of hydrogen. Thus, the OHP-enriched solvent produced by the process of the present invention provides not only improved coal solvation and an increased yield of distillate product, but it also provides reduced overall hydrogen consumption in a coal liquefaction process.

The solvent produced by the process of the present invention may additionally include Tetralin (1,2,3,4-tetrahydronaphthalene), as such material is normally found in phenanthrene-containing coal liquids and is an excellent hydrogen donor material. However, it has been found that because of the tendency of Tetralin to vaporize in the coal liquefaction step and reduce the hydrogen partial pressure, the hydrogen partial pressure of the liquefaction process can be increased if Tetralin is minimized or excluded by distillation from the solvent prior to OHP-enrichment by the process of the present invention. Accordingly, it may be desirable to prepare a substantially Tetralin-free OHP-enriched solvent for use in the liquefaction process.

BRIEF DESCRIPTION OF THE DRAWINGS

FIG. 2 graphically compares the solvation power of an OHP-enriched, hydrogenated solvent and an unhydrogenated process solvent as a function of hydrogen donor concentration at various temperatures;

FIG. 3 graphically illustrates the effect of increasing the level of OHP+T while decreasing the level of THP in a solvent for the liquefaction of coal; and FIG. 4 also illustrates the effect of increasing the level of OHP+T while decreasing the level of THP in a solvent for the liquefaction of coal.

DESCRIPTION OF THE PREFERRED EMBODIMENTS

Figure 1:
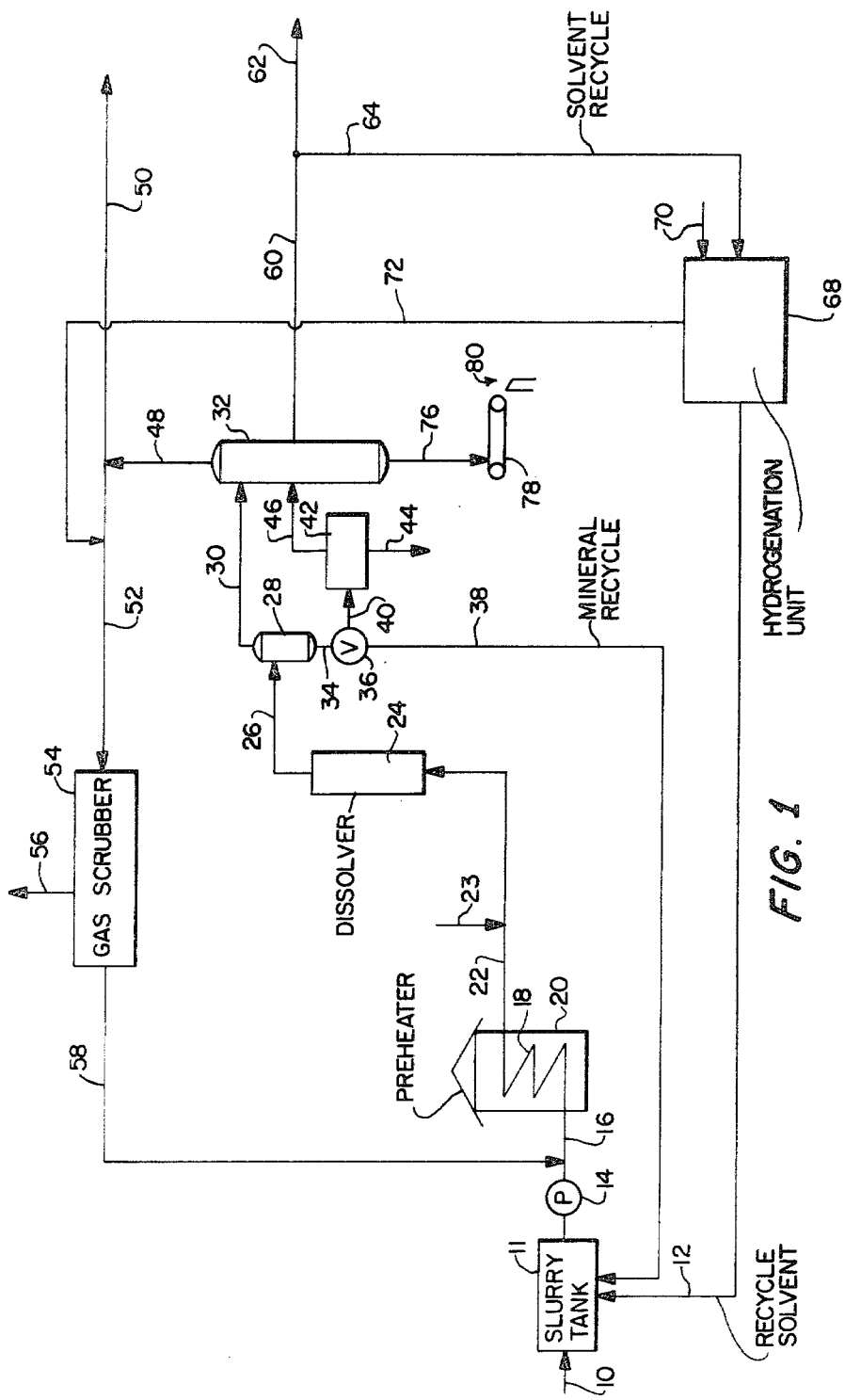
FIG. 1 is a schematic flow diagram of a process for the production of hydrocarbonaceous liquid fuel products from coal in accordance with the invention.

As shown in the process set forth in FIG. 1 of the drawings, pulverized raw coal is charged to the process through line 10 into a slurry tank 11 where the coal is combined with a hydrogen donor solvent introduced through line 12 and with or without recycled mineral from line 38, as hereinafter discussed, to form a feed slurry. Preferred coals include bituminous and subbituminous coals and lignites.

In accordance with the present invention, the solvent in line 12 contains a mixture of OHP and THP in a ratio of OHP to THP greater than 0.4 and preferably greater than 1, but less than 10 or 15. The OHP content of the solvent is at least 5 weight percent, and preferably at least about 10 weight percent based on the total weight of the solvent. The total concentration of OHP+THP+other hydrophenanthrenes and hydroanthracenes (if any)+P in the solvent is between about 10 and about 70 weight percent, preferably between about 20 and about 50 weight percent based upon the total weight of the solvent.

The OHP-enriched solvent stream is advantageously produced in a catalytic hydrogenation reactor 68 wherein a solvent containing a predetermined ratio of OHP to THP is produced by controlled catalytic hydrogenation of a coal-derived process solvent from a recycle fraction in the manner hereinafter described.

The feed slurry in tank 11 is pumped to process pressure by means of pump 14 and passed through process line 16 along with recycle hydrogen from line 58 to preheater tube 18 which is disposed in furnace 20. Preheater tube 18 preferably has a high length to diameter ratio of at least 100 or even at least 1000, to permit plug flow.

In the preheater stage, reaction between the OHP-enriched solvent and the coal results in swelling of the coal and in severing of hydrocarbon polymers from coal minerals. The maximum outlet preheater temperature can be between about 350° C. (662° F.) and about 500° C. (932° F.), preferably between about 400° C. (752° F.) and about 475° C. (877° F.). The residence time in preheater 20 is between about 0.01 to 0.5 hour, and preferably between about 0.01 and 0.15 hour.

The slurry effluent from preheater 20 is then passed through line 22 wherein additional hydrogen can be added, if desired, through line 23 in advance of dissolver 24. Following depletion of hydrogen and conversion of OHP to THP by donation of hydrogen to the coal, THP is reacted with gaseous hydrogen in dissolver 24 and reconverted to a limited extent to OHP. According to a preferred embodiment of the invention, coal minerals are recycled to the process as hereinafter described, because recycle coal minerals catalytically enhance the reconversion of THP to OHP in dissolver 24.

The temperature in the dissolver 24 is between about 350° C. (662° F.) and about 500° C. (932° F.), preferably between about 400° C. (752° F.) and about 475° C. (887° F.). The residence time in dissolver 24 is between about 0.1 and about 2.5 hours, preferably between about 0.15 and about 1.0 hour, and is longer than the residence time in the preheater.

The liquid space velocity for the liquefaction process (volume of slurry per hour per volume of liquefaction reactor) can range from 0.01 to 8.0, generally, and 0.5 to b 3.0, preferably. The ratio of hydrogen to slurry in the liquefaction zone can range from 200 to 10,000 standard cubic feet per barrel, generally, and 500 to 5000 standard cubic feet per barrel, preferably (3.6 to 180, generally and 9 to 90, preferably, SCM/100 L). The weight ratio of recycle solvent to raw coal in the feed slurry can range from 0.5:1 to b 5:1, generally, and from 1.0:1 to 2.5:1, preferably.

The reactions in both the preheater and dissolver stages occur in the presence of gaseous hydrogen and in both stages heteroatom sulfur and oxygen are removed from solvated deashed coal polymer, resulting in depolymerization and conversion of dissolved coal polymers to desulfurized and deoxygenated free radicals of reduced molecular weight. The free radicals have a tendency to repolymerize in the process but are stabilized against repolymerization by accepting hydrogen at the free radical site. Carbon monoxide and steam together with or in place of hydrogen can be utilized, since carbon monoxide and steam react to form hydrogen. The steam can be derived from moisture contained in the coal or can be injected as water.

The hydrogen partial pressure is between about 500 and about 4000 pounds per square inch (35 to 280 kg/cm$^2$), preferably between about 1000 and about 2000 pounds per square inch (70 to 140 kg/cm$^2$).

The total residence time for solvation/liquefaction is between about 3 minutes and about 3 hours, preferably between about 3 minutes and about 1.5 hour. If coal minerals recycle is utilized, the total residence time is between about 0.5 and about 1.5 hour.

The slurry leaving dissolver 24 passes through line 26 to flash chamber 28. Liquid and gaseous material is removed overhead from flash chamber 28 through line 30 and passed to distillation column 32. A slurry containing normally solid deashed coal, undissolved coal and coal minerals (ash) is removed from the bottom of flash chamber 28 by means of line 34, and a portion of this material may be passed by means of 3-way valve 36 through line 38 for recycle to the solvation/liquefaction process to enhance hydrogenation reactions and thereby enrich the OHP content in the process slurry. Some or all of the ash-containing solid fuel is fed by means of line 40 to filter 42 and separated ash removed through line 44. The filtrate is removed from filter 42 by means of line 46 and passed to distillation column 32.

Gases, including hydrogen for recycle, are removed overhead from distillation column 32 by means of line 48 and are either withdrawn from the process through line 50 or passed through line 52 to as scrubber 54 to separate impurities, such as hydrogen sulfide, ammonia and water vapor, which are removed through line 56, and to prepare a purified hydrogen stream for recycle pass through line 58.

A distillate liquid product of the process is removed from distillation column 32 by means of line 60. The process produces sufficient liquid to be withdrawn as a liquid fuel product 62, and still provide recycle liquid for use as a process solvent, which is recycled through line 64 for further treatment.

According to the present invention, the OHP depleted solvent in line 64 is passed to hydrogenation unit 68 along with hydrogen supplied by means of line 70 to provide the desired OHP to THP ratio in the hydrogen donor solvent.

The fraction of reactor effluent utilized as recycle solvent in line 64 has a boiling range between about 200° and about 500° C. (392° and 932° F.), preferably between about 280° and about 400° C. (537° and 752° F.).

The recycle fraction comprises naphthalene, Tetralin, and P, as well as THP and OHP. However, the weight ratio of OHP to THP in line 64 is less than 0.4; e.g., 0.19 or 0.22, and thus, such fraction must be subjected to catalytic hydrogenation in unit 68 under conditions to provide the desired ratio of OHP to THP.

Hydrogenation unit 68 contains a suitable hydrogenation catalyst comprising supported Group VIB and Group VIII metals, as oxides and/or sulfides. A preferred catalyst of the present invention is a tungsten-containing catalyst containing between about 5 and about 30 weight percent tungsten, preferably between about 15 and about 25 weight percent tungsten based upon the total catalyst weight. Such catalyst may be a NiW catalyst and may contain, for example, between about 5 and about 25 weight percent tungsten, preferably between about 10 and about 20 weight percent tungsten, and between about 5 and about 25 weight percent nickel, preferably between about 6 and about 20 weight percent nickel based upon the total catalyst weight. A particularly preferred catalyst is a NiWF catalyst which comprises 20 weight percent nickel, 20 weight percent tungsten and 2 weight percent fluorine.

The presence of tungsten coupled with the use of proper process conditions, such as an elevated hydrogen pressure, is necessary to achieve a ratio of OHP to THP greater than 1 in the solvent. Additionally, it is especially preferred to include titanium in the catalyst in an amount of between about 1 and about 10 weight percent, of the catalyst so as to improve hydrogen selectivity and economy as evidenced by a high aromatics level solvent. The term "aromatics" as used throughout this application means those compounds having an aromatic moiety whether they are partially saturated, such as OHP and THP, or not, such as P. The combination of tungsten and titanium produces a high OHP level solvent, but retains a high aromatics level as well. It is desirable to maintain at least 75 to 80 weight percent aromatics in the hydrogenated solvent. A lower level of aromatics would indicate that too much perhydrophenanthrene is produced as a by-product while achieving an OHP to THP ratio above 1, and this would greatly reduce the hydrogen-transfer capability of the solvent. Moreover, too great a loss of aromatics is costly in terms of hydrogen used, since hydrogen is very expensive. An especially preferred solvent hydrogenation catalyst for achieving these advantageous results is a NiTiMoW on alumina catalyst comprising between about 3 and about 10 weight percent nickel, between about 3 and about 10 weight percent titanium, between about 5 and about 15 weight percent molybdenum and between about 5 and about 15 weight percent tungsten based upon the total catalyst weight. A particularly preferred catalyst is a NiTiMoW on alumina catalyst which comprises 6 weight percent nickel, 5 weight percent titanium, 10 weight percent molybdenum and 10 weight percent tungsten based upon the total catalyst weight.

Any suitable support material may be employed, including those conventionally used for hydrogenation processes, such as the refractory inorganic oxides including alumina, silica, zirconia, titania, magnesia, thoria, boria and the like, or combinations thereof. The preferred support is a non-cracking support, such as alumina.

Suitable hydrogenation reaction conditions for hydrogenation unit 68 include temperatures between about 260° C. (500° F.) and about 427° C. (800° F.), preferably between about 340° C. (644° F.) and about 385° C. (725° F.). Suitable hydrogen partial pressures include those in the range of between about 1000 and about 2500 pounds per square inch (70 to 175 kg/cm$^2$), preferably between about 2000 and about 2500 pounds per square inch (140 to 175 kg/cm$^2$). In order to maximize the conversion of THP to OHP in unit 68 relatively high hydrogen partial pressures are utilized, and thus, especially preferred hydrogen partial pressures are in those in the range between about 2200 and about 2500 pounds per square inch (154 to 175 kg/cm$^2$). The liquid hourly space velocity can be between about 0.2 and about 10, generally, or between about 0.2 and 2.0 preferably, with 1.0 being especially preferred.

Hydrogen is withdrawn from hydrogenation unit 68 through line 72 and preferably passed to line 52 to join hydrogen recycle back to the coal solvation/liquefaction process.

The OHP-enriched solvent is withdrawn from unit 68 by means of line 12. The solvent now contains OHP and THP in a weight ratio greater than 0.4, and preferably greater than 1, but less than 10 or 15. The solvent contains at least 5 weight percent OHP, between about 5 and about 50 weight percent OHP, preferably between about 10 and about 30 weight percent OHP, and between about 5 and about 20 weight percent THP, preferably between about 10 and about 20 weight percent THP. Additionally, the solvent may contain between about 5 and about 30 weight percent Tetralin, preferably between about 10 and about 20 weight percent Tetralin, and between about 7 and about 15 weight percent P, preferably between about 5 and about 10 weight percent P. The foregoing percentages are based upon the total weight of the recycle solvent in stream 12.

It is especially preferred that the solvent contain OHP and THP in a ratio greater than 1, since with this ratio less hydrogen is consumed in the overall process including both the coal liquefaction and the catalytic hydrogenation zones, as compared with the use of OHP-enriched solvents containing OHP and THP in a ratio less than 1, even when such ratio is greater than 0.4.

The OHP-enriched solvent is passed by means of line 12 to slurry tank 11 to dissolve pulverized coal in the next pass. Preferably, a portion of the flash slurry containing coal minerals in line 34 is passed to line 38 by means of three-way valve 36 for recycle to slurry tank 11 along with the OHP-enriched solvent in line 12.

The recycle of the coal minerals induces an enhanced concentration of OHP in the solvent boiling range liquid circulating in the process. Recycle of coal minerals can achieve a given level of OHP within the liquefaction zone using a shorter liquefaction zone residence time as compared with a similar solvation/liquefaction process in which coal minerals are not recycled. Therefore, recycle of coal minerals cooperates with the catalytic hydrogenation step to increase the OHP/THP ratio within the process. Also, recycle of coal minerals induces a higher concentration of Tetralin in the liquid solvent as compared with a similar process without minerals recycle.

The recycled coal minerals act as a catalyst for the hydrogenation reactions occurring in the liquefaction zone. In addition, normally solid dissolved coal accompanies the coal minerals in line 38 and is advantageously converted to lighter materials by recycle.

The non-recycled portion of the flash residue from line 34 is passed to distillation column 32, which may be a vacuum column. Vacuum bottoms (deashed solid coal) product is removed from distillation column 32 through line 76 and passed to a moving conveyor belt 78, on which it is cooled and solidifed and from which it is removed by a suitable belt scraper means, as indicated at 80.

The following examples illustrate the invention, and are not intended to limit the invention, but rather, are presented for purposes of illustration. All percentages are by weight unless otherwise indicated, and the quantity of metal in the catalyst is reported as elemental metal.

EXAMPLE 1

Tests were conducted to compare the activity of various catalysts for the production of an OHP-enriched solvent utilizing as feed to the hydrogenation reactor a process solvent having the following inspections:

| | | |
|---|---|---|
| Elemental Analysis, wt. % | | |
| Carbon | 87.53 | |
| Hydrogen | 7.82 | |
| Sulfur | 0.81 | |
| Nitrogen | 0.95 | |
| Oxygen | 3.41 | |
| Gravity, Degrees API | 2.4 | |
| Saturates, wt. % | 4.6 | |
| Distillation D86 | | |
| °C., (°F.) | | |
| O.P. | 234 | (453) |
| 10% | — | — |
| 30% | 267 | (513) |
| 50% | 294 | (561) |
| 70% | 335 | (635) |
| 90% | 401 | (754) (84%) |
| EP | — | — |

Separate portions of the aforesaid process solvent were hydrogenated in independent hydrogenation runs each using a fixed-bed reactor at a temperature of 371° C. (700° F.) employing a hydrogen rate of 5000 SCF/barrel (890 cubic meters/cubic meter) at a liquid hourly space velocity of 1.0. The catalyst of one run was NiTiMo/Al$_2$O$_3$ and contained 3 percent by weight nickel, 5 percent by weight titanium and 8 percent molybdenum on alumina. A second catalyst utilized was NiCoMo/Al$_2$O$_3$ which contained 1 percent by weight nickel, 3 percent by weight cobalt and 12 percent by weight molybdenum on alumina. A third catalyst used was NiWF/Al$_2$O$_3$ containing 20 percent by weight nickel, 20 percent by weight tungsten and 2 percent by weight fluorine on alumina. A fourth catalyst used was NiTiMoW/Al$_2$O$_3$ and contained 6 percent by weight nickel, 5 percent by weight titanium, 10 percent by weight molybdenum and 10 percent by weight tungsten on alumina. All of the catalysts were tested at 2200 psig (154 kg/cm$^2$), and in addition, the NiTiMoW catalyst was tested in runs using pressures of 1000 psig (70 kg/cm$^2$) and 1500 psig (105 kg/cm$^2$), respectively.

Each catalyst was presulfided with a blend of 9.8 volume percent of hydrogen sulfide and 90.2 volume percent hydrogen at atmospheric pressure and 600° F. (316° C.) for four hours.

The catalysts exhibited the following activities for OHP enrichment:

5 (83.4). A low level of aromatics indicates a reduced hydrogen selectivity and the production of perhydrophenanthrenes and perhydroanthracenes, which are not hydrogen donors. The results set forth in Table I demonstrate that a tungsten-containing catalyst can provide a high OHP to THP ratio, and the addition of titanium thereto maintains a high aromatics level in the solvent (high hydrogen selectivity).

A further advantage of the combination of tungsten and titanium as in Test 5 is the achievement of the highest OHP+Tetralin yield of all the tests, Tetralin being a

TABLE I

| Test | 1 | 2 | 3 | 4 | 5 | 6 | 7 | 8 |
|---|---|---|---|---|---|---|---|---|
| Catalyst | — | NiTiMo | NiCoMo | NiWF | NiTiMoW | NiTiMoW | NiTiMoW | Pyrite |
| Pressure, psig | — | 2200 | 2200 | 2200 | 2200 | 1000 | 1500 | — |
| (kg/cm$^2$) | | (154) | (154) | (154) | (154) | (70) | (105) | |
| Aromatics, wt. % of solvent | 95.8 | 86.6 | 85.2 | 80.7 | 83.4 | 92.4 | 89.4 | 91.7 |
| Mass Spec Analysis, wt. % of solvent | | | | | | | | |
| Octahydrophenanthrene (OHP) | 3.7 | 12.2 | 10.7 | 13.4 | 13.2 | 8.0 | 10.6 | 4.3 |
| Tetrahydrophenanthrene (THP) | 19.5 | 14.6 | 14.7 | 11.4 | 12.9 | 17.6 | 15.6 | 18.3 |
| Phenanthrene(P) | 7.2 | 2.5 | 2.6 | 1.3 | 1.8 | 3.9 | 2.7 | 6.4 |
| Tetralin (T) | 6.5 | 16.7 | 18.1 | 18.0 | 20.8 | 15.2 | 17.7 | 9.1 |
| Naphthalene (N) | 12.5 | 3.4 | 4.0 | 2.3 | 3.2 | 8.3 | 4.7 | 6.2 |
| OHP + T | 10.2 | 28.9 | 28.8 | 31.4 | 34.0 | 23.2 | 27.7 | 13.4 |
| (OHP + T)/(THP + P + N) | 0.26 | 1.41 | 1.35 | 2.09 | 1.90 | 0.78 | 1.23 | 0.43 |
| OHP/THP | 0.19 | 0.84 | 0.73 | 1.17 | 1.02 | 0.45 | 0.68 | 0.23 |

Test 1 sets forth the OHP and THP content (as well as the contents of other materials) of the recycle solvent in a process which did not employ a catalytic hydrogenation step and indicates that the rate of OHP to THP in the absence of catalytic hydrogenation is 0.19. The solvent of Test 1 was obtained from a product fraction produced by a process of the type shown in FIG. 1, except that mineral residue was not recycled and there was no catalytic hydrogenation zone. Test 8 sets forth the analysis of an OHP-contaning solvent produced utilizing a process such as that shown in FIG. 1 employing mineral residue recycle but without a catalytic hydrogenation zone. The data of Test 8 show that recycle of minerals extracted from coal provides a solvent having a greater OHP/THP ratio (0.23), as compared to the OHP/THP ratio in a process solvent (Test 1) obtained in the absence of mineral residue recycle (0.19).

Table I shows that the tungsten-containing catalysts if Tests 4 and 5 were the most active for producing OHP, and provided a ratio of OHP to THP greater than 1, specifically, 1.17 and b 1.02, respectively.

Additionally, Table I shows that with a given catalyst an increasing level of OHP is produced with an increasing hydrogen pressure in the catalytic zone as demonstrated by the OHP produced in Tests 5, 6 and 7.

Test 5 shows that the addition of tungsten to the NiTiMo catalyst of Test 2 increased the ratio of OHP to THP to a level greater than 1 from a level below 1. It is significant that the relatively low aromatics content of the solvent obtained using the titanium-free tungsten-containing catalyst of Test 4 (80.7) was improved by the addition of titanium to the catalyst as indicated in Test highly desirable hydrogen donor.

EXAMPLE 2

Tests were conducted to compare the activity of the OHP-enriched process solvents of Example 1 produced by catalytic hydrogenation by employing these solvents in a coal liquefaction process feeding a 200-mesh Kentucky No. 9 coal having the following inspections:

| Elemental Analysis, wt. % | |
|---|---|
| Carbon | 70.66 |
| Hydrogen | 5.35 |
| Sulfur | 3.25 |
| Nitrogen | 1.52 |
| Oxygen | 15.55 |
| Moisture, wt. % | 3.31 |
| Ash, wt. % | 9.12 |
| Particle Size, mesh | wt. % |
| >200 | 7.0 |
| 200–325 | 26.8 |
| 325–625 | 36.3 |
| <625 | 29.9 |

Each of the solvents produced in Tests 1–8 as reported in Table I was admixed with a portion of the aforesaid coal, and each coal-solvent admixture was separately charged to a batch rocking autoclave at a coal/solvent weight ratio of 40/60 employing a temperature of 800° F. (427° C.) in the presence of hydrogen under a pressure of 1000 or 2000 psig (70 kg/cm$^2$, 140 kg/cm$^2$) and a residence time of one hour. The autoclave was unloaded and the sample was subjected to analysis. The results are shown in Table II, below:

TABLE II

| Test | 1 | 2 | 3 | 4 | 5 | 6 | 7 | 8 | 9 |
|---|---|---|---|---|---|---|---|---|---|
| Pressure, psig | 2000 | 2000 | 2000 | 2000 | 2000 | 2000 | 1000 | 2000 | 1000 |
| (Kg/cm$^2$) | (140) | (140) | (140) | (140) | (140) | (140) | (70) | (140) | (70) |
| Hydrogen Added, wt. % of coal | 4.9 | 5.9 | 6.1 | 4.6 | 4.8 | 5.5 | 2.4 | 4.8 | 2.4 |
| Aromatics, wt. % of solvent | 95.8 | 86.9 | 86.3 | 87.2 | 87.7 | — | 92.6 | 91.7 | 94.8 |
| Mass Spec Analysis, | | | | | | | | | |

TABLE II-continued

| Test | 1 | 2 | 3 | 4 | 5 | 6 | 7 | 8 | 9 |
|---|---|---|---|---|---|---|---|---|---|
| wt. % of solvent fraction | | | | | | | | | |
| Octahydro-phenanthrene (OHP) | 3.6 | 6.0 | 6.1 | 5.9 | 5.8 | — | 2.7 | 4.1 | 2.7 |
| Tetrahydro-phenanthrene (THP) | 21.2 | 19.0 | 17.7 | 17.3 | 17.8 | — | 19.5 | 18.4 | 17.6 |
| Phenanthrene (P) | 7.1 | 4.2 | 3.7 | 2.8 | 3.2 | — | 7.3 | 6.7 | 7.3 |
| Tetralin (T) | 7.5 | 12.3 | 13.8 | 14.5 | 14.0 | — | 8.2 | 8.1 | 6.4 |
| Naphthalene (N) | 11.3 | 6.5 | 7.3 | 7.5 | 6.5 | — | 13.2 | 6.8 | 14.6 |
| OHP + T | 11.1 | 18.3 | 19.9 | 20.4 | 19.8 | — | 10.9 | 12.2 | 9.1 |
| (OHP + T)/(THP + P + N) | 0.28 | 0.62 | 0.69 | 0.74 | 0.72 | — | 0.27 | 0.38 | 0.23 |
| OHP/THP | 0.17 | 0.32 | 0.34 | 0.34 | 0.33 | — | 0.14 | 0.22 | 0.15 |
| % Solvation (MAF) | 91.3 | — | 86.9 | 90.7 | 89.1 | 90.6 | 89.0 | 91.3 | 78.8 |
| % Hydrocracking (MAF) | 17.1 | — | 18.6 | 32.5 | 30.2 | 18.3 | 24.4 | 24.0 | 4.5 |
| % Distillation Residue (wt. % of filtrate) | 26.7 | — | 22.1 | 21.1 | 21.1 | 25.8 | 24.7 | 24.8 | 30.1 |

The material balance obtained was 98 percent or better in each case. The "Hydrogen Added" in Table II is the hydrogen added in the coal liquefaction zones.

Tests 1–6 and 8 in Table II were made using the corresponding solvent reported in Tests 1–6 and 8 in Table I of Example 1. Test 7 of Table II was made using the solvent of Test 6 of Table I. Test 9, like Test 1, employed a recycle solvent from a coal liquefaction process that did not employ either a catalytic hydrogenation step or mineral recycle.

The test results of Table II show that in Tests 1–5, the OHP content of the solvent fraction following liquefaction dropped in each case as compared with the OHP content of the feed solvent used to dissolve the coal, shown in Tests 1–5 in Table I. Moreover, the THP content of each solvent increased during liquefaction, thus demonstrating that the OHP is a much more active hydrogen donor during liquefaction than is THP, and OHP is converted to THP without an appreciable or comparable conversion of THP to a lower hydrogen level.

Additionally, in Tests 4 and 5, where the feed solvent contained a ratio of OHP to THP greater than 1, the OHP content of the solvent dropped to a greater extent during liquefaction, i.e., 56 percent in both Test 4 and Test 5, than did the feed solvents of Tests 2 (51 percent) and 3 (43 percent) wherein the OHP/THP ratio was less than 1. This shows that a high OHP/THP ratio in the feed solvent is conductive to a high level of hydrogen donation in the liquefaction step. Moreover, the OHP concentration of each solvent dropped even more than did the Tetralin content of the respective solvent. For example, the OHP concentration of the solvent dropped 56 percent in Test 5, whereas the Tetralin content of the Test 5 solvent dropped only 32.7 percent by weight. Similarly, in Test 4 the OHP concentration dropped 56 percent, while the Tetralin content dropped only 19.4 percent by weight. Thus, the OHP was a significantly more active hydrogen donor than was the Tetralin.

Also, it is noted that the present solvation of the coal was greater in Tests 4 and 5, wherein the OHP/THP was greater than 1, as compared with Test 3, for example, where the OHP/THP ratio was less than 1, thus further indicating that the solvents of Tests 4 and 5 induce improved hydrogen transfer as compared to the solvent of Test 3. Likewise, the degree of hydrocracking was greater during liquefaction when using the test solvents of Tests 4 and 5 as compared with the solvent of Test 3, which indicates improved production of liquid product.

Tests 6 and 7 both utilized the same solvent for coal liquefaction, which solvent is reported in Test 6 of Table I, but different liquefaction pressures. Test 6 employed a pressure of 2000 psig, while Test 7 employed a pressure of 1000 psig. The results of Tests 6 and 7 indicate that while hydrogen pressure affects hydrogen donor concentration significantly in the catalytic step, its effect upon coal liquefaction in the presence of a prehydrogenated solvent in which the OHP content has been enhanced, is small. Thus, there is little difference in the percent solvation or hydrocracking between Tests 6 and 7, wherein a liquefaction pressure of 2000 psi and 1000 psi were used, respectively. However, when comparing Tests 1 and 9, wherein the same unhydrogenated solvent was used, but at liquefaction pressures of 2000 and 1000 psi, respectively, the differences in percent solvation and hydrocracking were much greater. These data indicate that the OHP/THP ratio of this invention relieves the liquefaction process of a high sensitivity to hydrogen pressure, so that the hydrogen off-gas from the catalytic hydrogenation zone, which is reduced in pressure, can be advantageously utilized in the coal liquefaction process. Therefore, as shown in FIG. 1 fresh hydrogen under pressure is introduced through line 70 directly to unit 68, which is sensitive to hydrogen pressure, before reaching the liquefaction zone via line 72.

Tests 4 and 5 of Table II show a further significant advantage in the use of a solvent having the high OHP/THP ratio of this invention, because the product from Tests 4 and 5 contains the lowest level of non-hydrogenated P of all the tests. A low level of P indicates that the THP in the system did not tend to become further dehydrogenated to P, so that the THP was available for recycle to the catalytic hydrogenation zone for rehydrogenation to OHP. Apparently, with a high OHP/THP ratio in the solvent, the OHP assumes the hydrogenation function and less active THP is relieved of this function. In the present invention the liquefaction residence time is sufficiently low that the THP does not assume a significant hydrogen donation function.

EXAMPLE 3

In order to demonstrate the effect of employing an OHP-enriched solvent for coal liquefaction at elevated temperatures, a series of tests was conducted to determine the effect upon coal solvation of a catalytically hydrogenated, OHP-enriched solvent as compared with an unhydrogenated solvent at various hydrogen donor concentrations. The hydrogenated solvent of Example 1 was subjected to catalytic hydrogenation using a NiTiMoW/Al$_2$O$_3$ catalyst at 700° F. (371° C.) under a hydrogen pressure of 1000 psig (70 kg/cm$^2$). Separate portions of the hydrogenated solvent, and of the unhydrogenated solvent of Example 1, were utilized for coal liquefaction employing the feed coal of Example 2 at temperature of 800° F. (427° C.), 825° F. (441° C.) and 850° F. (454° C.), respectively, all under a hydrogen pressure of 1000 psig (70 kg/cm$^2$). Following are the results of these tests:

TABLE III

| Temperature °F. (°C.) | Coal Solvation, Wt. % MAF Coal | |
|---|---|---|
| | Unhydrogenated Solvent (10 wt. % OHP + T) | Hydrogenated Solvent (17 wt. % OHP + T) |
| 800 (427) | 78.8 | 83.5 |
| 825 (441) | 82 | 85.0 |
| 850 (454) | 57 | 80 |

The data in Table III are presented graphically in FIG. 2.

FIG. 2 shows that the advantage in coal solvation of using the prehydrogenated solvent is more pronounced when the liquefaction temperature is 850° F. (454° C.), as compared to 800° F. (427° C.) or 825° F. (441° C.) at a common hydrogen pressure of 1000 psig (70 kg/cm$^2$). The reason is that repolymerization is more likely to occur at 850° F. (454° C.) and 1000 psig (70 kg/cm$^2$), thereby reversing the depolymerization coal solvation reaction.

EXAMPLE 4

Tests were conducted in which a heavy distillate fraction that had been produced in a coal solvation/liquefaction process in which coal minerals were recycled, was used as the feed to a catalytic hydrogenation unit for OHP enrichment. The heavy distillate had the following inspections:

| Elemental Analysis, wt. % | | |
|---|---|---|
| Carbon | | 88.79 |
| Hydrogen | | 8.47 |
| Sulfur | | 0.49 |
| Nitrogen | | 1.04 |
| Oxygen | | 1.91 |
| °API | | 7.3 |
| Saturates, wt. % | | 9.8 |
| Distillation D86, °C. (°F.) | | |
| OP | 215 | (419) |
| 10% | 244 | (471) |
| 30% | 276 | (529) |
| 50% | 301 | (574) |
| 70% | 330 | (626) |
| 90% | 379 | (714) |
| EP | — | |

A sample of the heavy distillate was subjected to hydrogenation using a NiTiMoW/Al$_2$O$_3$ catalyst comprising 6 percent by weight nickel, 5 percent by weight titanium, 10 percent by weight molybdenum, 10 percent by weight tungsten, supported on alumina. Hydrogenation was performed at a temperature of 724° F. (384° C.) under a hydrogen pressure of 2200 psig (154 kg/cm$^2$) and with a liquid hourly space velocity of 1.0.

The mass spectrometric analysis of the hydrogenated solvent is set forth in Table IV, below, as Test 1. A sample of the hydrogenated solvent was utilized in coal liquefaction. It was admixed with pulverized Pittsburgh seam coal and the slurry was fed to an autoclave operated at a temperature of 850° F. (454° C.), a pressure of 2000 psig (140 kg/cm$^2$) for a residence time of 20 minutes.

A mass spec analysis of the solvent range fraction produced in the coal liquefaction is set forth as Test 2 in Table IV, below:

TABLE IV

| Test | 1 | 2 |
|---|---|---|
| Mass Spec Analysis, wt. % sample | | |
| Octahydrophenanthrenes (OHP) | 13.9 | 9.9 |
| Hexahydrodphenanthenes | 1.2 | 1.1 |
| Tetrahydrophenanthrenes (THP) | 12.0 | 17.6 |
| Phenanthrenes (P) | 1.5 | 3.2 |
| Tetralin (T) | 6.2 | 6.6 |
| OHP/THP | 1.16 | 0.56 |

The data in Table IV show that in the course of the liquefaction reaction the OHP content of the solvent range liquid dropped from 13.9 weight percent to 9.9 weight percent, while at the same time the THP content of the solvent increased. Additionally, the Tetralin content of the solvent increased from 6.2 weight percent to 6.6 weight percent. Thus, Table IV shows that Tetralin is being produced in the liquefaction reactor, while the OHP is being consumed, showing that the OHP is the most active hydrogen donor.

Of particular importance is the fact that the low liquefaction residence time of only 20 minutes assisted in keeping the OHP level relatively high, so that the solvent range liquid from the liquefaction zone still had a comparatively high OHP concentration (9.9 wt. %).

EXAMPLE 5

For comparative purposes a heavy distillate fraction similar to that of Example 4 which is not subjected to catalytic hydrogenation is used as a solvent in coal liquefaction employing mineral residue recycle. The solvent fraction is admixed with pulverized Pittsburgh seam coal and passed to an autoclave maintained at a temperature of 850° F. (454° C.), a pressure of 2000 psig (140 kg/cm$^2$) for a residence time of 20 minutes.

An analysis of the solvent fraction supplied to the liquefaction step and of a solvent fraction in the liquefaction effluent is set forth as Tests 1 and 2, respectively, in Table V below:

TABLE V

| Test | 1 | 2 |
|---|---|---|
| Mass Spec Analysis, wt. % sample | | |
| Octahydrophenanthrenes (OHP) | 2.1 | 2.4 |
| Hexahydrophenanthenes | 1.8 | 1.8 |
| Tetrahydrophenanthrenes (THP) | 17.3 | 17.5 |
| Phenanthrenes (P) | 6.4 | 6.4 |
| Tetralins (T) | 1.9 | 2.7 |
| OHP/THP | .12 | .14 |

The data of Table V demonstrate that the solvent produced in a liquefaction process utilizing mineral residue recycle can sustain its OHP and Tetralin levels even without catalytic hydrogenation, although at low levels.

EXAMPLE 6

In order to demonstrate the effect of OHP and Tetralin upon coal solvation, a series of tests were conducted utilizing two, separate hydrogenated solvents each containing OHP, T, THP and other hydroaromatics. One of the solvents contained about 22 percent OHP+T and about 39.5 percent THP and other hydroaromatics; the other solvent contained about 10 percent OHP+T and about 42.5 percent THP and other hydroaromatics. Each solvent was tested in a liquefaction process at two temperatures of 800° F. (427° C.) and 850° F. (454° C.), respectively. The pressure in all tests was 1000 psig (70 kg/cm$^2$). The results are set forth in Table VI and FIG. 3.

TABLE VI

| Temperature °F. (°C.) | Coal Solvation, Wt. % of MAF Coal | | | |
|---|---|---|---|---|
| | OHP + T (10 wt. %) | OHP + T (22 wt. %) | Others + THP (39.5 wt. %) | Others + THP (42.5 wt. %) |
| 800 (427) | 76 | 86 | 86 | 76 |
| 850 (454) | 57 | 80 | 80 | 57 |

FIG. 3 graphically illustrates the data of Table VI in terms of the level of particular aromatic components in the solvent.

FIG. 3 shows that the percent coal solvation increases as the concentration of OHP+Tetralin in the solvent (OHP+T) increases, but decreases when the concentration of other hydroaromatics in which THP predominates, increases at the expense of OHP. The increase in OHP+T needed for improving the coal solvation at 800° F. (427° C.) from 76 weight percent to 86 weight percent of the MAF coal is 12 percent of the total solvent, but is equivalent to a 120 percent increase in the OHP+T components themselves. Thus, FIG. 3 demonstrates that OHP+T constitutes a sensitive indicator for measuring the hydrogen transfer capability of a solvent for coal liquefaction. FIG. 3 shows that the dependence of coal solvation on OHP+T content is even more pronounced at higher temperatures, such as 850° F. (454° C.), then at lower temperatures 800° F. (427° C.).

EXAMPLE 7

In order to demonstrate the effect of the OHP content of the solvent upon distillate yield in a coal liquefaction process, tests were conducted utilizing four separate hydrogenated hydroaromatics-containing solvents for coal liquefaction at 800° F. (427° C.), and a hydrogen pressure of 2000 psig (140 kg/cm$^2$). An analysis of the distillate yield versus concentration of OHP+T for each of the four solvents and of the respective concentrations of the corresponding THP and other hydroaromatics in the solvents is set forth in Table VII, below:

TABLE VII

| Distillate Yield (wt. % of MAF Coal) | OHP + T (wt. % of solvent) | THP + Others (wt. % of solvent) |
|---|---|---|
| 13.5 | 10 | 42.5 |
| 20 | 13 | 36 |
| 29 | 34 | 31 |

The data in Table VII are presented graphically in FIG. 4 in a manner which illustrates the effect of interchanging OHP+T with THP and other hydroaromatics in a solvent. The ascending curve in FIG. 4 shows that the distillate yield increases as the weight percent of OHP+T in the solvent increases. In contrast, the descending curve shows that distillate yield decreases as the concentration of THP and other hydroaromatics increases at the expense of OHP+T. Distillate yield is greatly affected by the hydrogen transfer capability of the solvent, because production of distillate requires highly reactive hydrogen donors to inhibit polymerization of free radicals.

Although the invention has been described in considerable detail with particular reference to certain preferred embodiments thereof, variations and modifications can be effected within the spirit and scope of the invention as described herein before, and as defined in the appended claims.

What is claimed is:

1. A process for the production of an OHP-enriched solvent for use in coal liquefaction, which process comprises contacting a coal-derived liquid solvent, said solvent being coal liquefaction reactor effluent having a boiling range between about 200° and about 500° C. and consisting essentially of OHP, THP and P, said OHP and THP being present in a ratio of OHP/THP below 0.4, with hydrogen in the presence of a supported catalyst consisting essentially of Group VIB and Group VIII metals under hydrogenation conditions including a temperature between about 260° and about 427° C. to provide an OHP-enriched solvent containing OHP and THP in a ratio of OHP/THP greater than 0.4 and below 15, and at least 1 weight percent THP.

2. The process of claim 1, wherein said catalyst comprises tungsten.

3. The process of claim 2, wherein said catalyst additionally comprises titanium.

4. The process of claim 3, wherein said catalyst is provided with an alumina support.

5. The process of claim 3, wherein said OHP-enriched solvent contains OHP and THP in a ratio of OHP/THP greater than 1 and wherein said OHP-enriched solvent contains at least 5 weight percent OHP.

6. The process of claim 5, wherein the OHP-enriched solvent contains between about 5 and about 10 weight percent P.

7. The process of claim 2, wherein said catalyst comprises either NiWF or NiTiMoW.

8. The process of claim 7, wherein said catalyst comprises NiTiMoW.

9. The process of claim 2, wherein said catalyst contains between about 10 and about 20 weight percent tungsten and between about 6 and about 20 weight percent nickel based upon the total catalyst weight.

10. The process of claim 1, wherein said process is conducted at a temprature in the range between about 340° and 385° C. at a hydrogen partial pressure in the range between about 1000 and about 2500 psi.

11. The process of claim 10, wherein said hydrogenation pressure is between about 2000 and about 2500 psi.

12. The process of claim 1, wherein the feed to said process comprises a distillate liquid boiling in the range between about 280° and about 400° C.

13. The process of claim 1 wherein said OHP-enriched solvent contains below about 10 weight percent P.

14. The process of claim 1, wherein said OHP-enriched solvent contains OHP and THP in a ratio of OHP/THP between about 1 and about 10.

15. The process of claim 1, wherein said fraction has a boiling range between about 280° and about 400° C.

16. The process of claim 1, wherein said supported catalyst is NiWF.

17. The process of claim 16, wherein said catalyst support is alumina.

18. The process of claim 1, wherein said catalyst is NiTiMoW on an alumina support.

19. The process of claim 1, wherein said OHP-enriched solvent contains between about 10 to 20 weight percent THP.

* * * * *

UNITED STATES PATENT OFFICE
CERTIFICATE OF CORRECTION

Patent No. 4,312,746　　　　　　　　Dated　January 26, 1982

Inventor(s) Shirley C. Tsai and Howard G. McIlvried, III

It is certified that error appears in the above-identified patent and that said Letters Patent are hereby corrected as shown below:

Column 3, line 29, "perhydroanthrenes" should be --perhydroanthracenes--.

Column 4, line 58, "877° F." should be --887° F.--.

Column 5, line 64, "as" should be --gas--.

Column 11, line 60, "present" should be --percent--.

Column 13, line 3, "hydrogenated" should be --unhydrogenated--.

Signed and Sealed this

Twenty-third Day of November 1982

[SEAL]

Attest:

GERALD J. MOSSINGHOFF

Attesting Officer　　　Commissioner of Patents and Trademarks